United States Patent [19]

Shanbrom

[11] Patent Number: 5,128,149
[45] Date of Patent: Jul. 7, 1992

[54] ENHANCED BLOOD PRODUCT ANTIVIRAL PROCESS AND PRODUCT PRODUCED

[76] Inventor: Edward Shanbrom, 2252 Liane La., Santa Ana, Calif. 92705

[21] Appl. No.: 424,682

[22] Filed: Oct. 20, 1989

Related U.S. Application Data

[63] Continuation-in-part of Ser. No. 321,522, Mar. 9, 1989, abandoned, and a continuation-in-part of Ser. No. 290,161, Dec. 28, 1988, Pat. No. 4,891,221, and a continuation-in-part of Ser. No. 276,113, Nov. 23, 1988, abandoned.

[51] Int. Cl.$^5$ .............................................. A61K 35/14
[52] U.S. Cl. .................................. 424/529; 424/530; 424/533; 435/2
[58] Field of Search ............... 424/529, 530, 531, 532, 424/533, 534; 435/2

[56] References Cited

PUBLICATIONS

Shah et al-Chem. Abst. vol. 100 (1984) p. 56697h.
Yonezawa et al.-Chem. Abst. vol. 103 (1985) p. 76065r.
Yonezawa et al.-Chem. Abst. vol. 98 (1983) p. 185483z.
Shiseido-Chem. Abst. vol. 100 (1984) p. 161681w.

*Primary Examiner*—Sam Rosen
*Attorney, Agent, or Firm*—Grant L. Hubbard

[57] ABSTRACT

A transfusion blood product container for the introduction of one or more blood products, such as whole blood, platelet concentrations, leukocyte concentrations, plasma, phasma derivatives, whole blood fractions, and combinations thereof, for transfusing the patient and an amount of one or more glycyrrhizic triterpenoid compounds sufficient to comprise from 0.05 to 10.0 wt/%, preferably from about 0.5 to about 3 wt/%, of the contents of the container when full of the blood product(s), sufficient to substantially inactivate viruses contained in the blood product introduced into said container is disclosed. One or more additional products are added to the glycyrrhizic triterpenoid compounds to produce a synergistic affect.

31 Claims, No Drawings

ENHANCED BLOOD PRODUCT ANTIVIRAL PROCESS AND PRODUCT PRODUCED

CROSS-REFERENCE TO RELATED APPLICATION

This is a continuation-in-part of my copending U.S. patent applications Ser. No. 07/321,522, filed Mar. 9, 1989, now abandoned, Ser. No. 07/290,161, Filed Dec. 28, 1988, now U.S. Pat. No. 4,891,222, and Ser. No. 07/276,113, filed Nov. 23, 1988, now abandoned, to which priority is claimed.

FIELD OF THE INVENTION

This invention relates to the treatment of mammalian biological cells and fluids with one or more of a class of compounds referred to here as glycyrrhizic compounds, exemplary of which are glycyrrhizin, glycyrrhizinic acid or glycyrrhetinic acid glycoside, and analogous triterpenes, e.g. carbenoxolone and cicloxolone and their derivatives, to inactivate virus and to improved containers for providing such treatment.

BACKGROUND OF THE INVENTION

This invention relates to the treatment of whole blood to inactivate or destroy infective viruses found in animal fluids and cells, such as the cytomegalovirus which is responsible for or aggravates serious and sometimes fatal infections, in blood transfusion recipients. The term "inactivate" as applied to the inactivation of virus in accordance with the present invention means that the virus are rendered non-infectious to the patient. In some instances, virus cultures may still be viable for a period of time, but lack the ability to pathogenically infect a patient.

Cytomegalovirus (CMV) is probably the most ubiquitous of the pathogenic viruses found in animal fluids and tissues. Virtually all of the people living in the developing countries become infected with CMV early in life, and CMV infects over half the population in the developed countries of the world. CMV may remain essentially inactive in the body following an initial infection and may flare in to an active infection any time, most frequently when the body's immune system is compromised to a greater or lesser degree by disease, radiation therapy, drug therapy, surgical trauma, etc. CMV is frequently associated with, and may be a causative or contributing factor in, lifethreatening disease in individuals with suppressed immune systems, and can be a principal causative factor in pneumonia, neurological disorders, febrile illness, ocular disease and hepatitis. CMV infection is a serious limiting factor in the transplantation of organs, tissues and cells and the transfusion of blood and plasma from one individual to another. The kidney transplant patient runs a high risk of contracting serious, and not infrequently fatal, CMV infection from CMV introduced by the transplant organ. Recipients of whole blood, plasma, bone marrow, cornea, cardiac, and semen run a serious risk of CMV infectious disease, the risk being multiplied where the immune system of the recipient is suppressed to prevent rejection of the foreign organ or cells, or where immunosuppression is present from natural causes.

CMV is frequently associated with *Pneumoncystis carinii* and may cause or contribute to encephalitis and colitis and may be associated with Kaposi's sarcoma in AIDS patients. CMV is so ubiquitous in the blood and organs of donors who, frequently, exhibit no symptoms of infection, and its direct and contributory effects in infectious diseases is so pervasive and subtle that a CMV infection is to be presumed if another causative agent cannot be established.

There are no proven cures or generally effective drugs for the treatment of CMV infections. Certain drugs, e.g. ganciclovir, has been shown to have limited effectiveness in the treatment of certain CMV infections, e.g. CMV retinitis, but has little effect in the treatment of CMV pneumonia. Live attenuated CMV vaccine has been developed but may not protect against infection by natural CMV, and there is a real risk that the attenuated CMV may reactivate during pregnancy and infect the fetus.

While a method of preventing, or even reducing the likelihood of transmitting CMV via transfusion or transplant of organs, tissues, cells or fluids would be of enormous benefit to medical science, the present invention is not limited to treatments to inhibit CMV infection and is applicable to other classes of viruses found in animal fluids and tissues.

CMV is a member of the human herpesvirus (HV) group, which are responsible for much of mankind's discomfort and pain. The herpesviruses represent a very large, clearly defined group of viruses which are responsible for, or involved in, cold sores, shingles, a venereal disease, mononucleosis, eye infections, birth defects and probably several cancers. Three subfamilies are of particular importance. The alpha subfamily includes HV-1 (herpes virus simplex 1) which causes cold sores, fever blisters, eye and brain infections, HV-2 (herpes virus simplex 2) which cause genital ulceration, and HV-3 (HV varicella zoster) which causes chicken pox, shingles and brain infections. The beta subfamily includes HV-5, the principal member of which is CMV discussed above. The gamma subfamily includes HV-4 (Epstein-Barr) which cause infectious mononucleosis and is involved in Burkitt's lymphoma and nasopharyngeal carcinoma. Additional possibly pathogenic herpes viruses no doubt exist, one type of which, HV-6, of unknown pathogenicity has been identified. (Niederman, J. C. et al., The Lancet, Oct. 8, 1988, 817). There is evidence that the methods of this invention are effective in inhibiting the transmission of infections caused by many and perhaps all of the pathogenic herpes viruses found in animal fluids and tissues.

While blood bankers have instituted rigid criteria for exclusion of potential donors in high risk categories, this is not a satisfactory solution to the most significant threat to face the health care community in many decades. Institution of human immunodeficiency virus (HIV) testing has blood products safer, but the complete elimination of HIV contaminated blood and blood products has not been possible using present knowledge and technology. The ELISA test, for example, misses approximately 1 in 200 (0.5%) HIV infected donors, and there is no certain method for excluding donor carriers of hepatitis and other infectious viruses found in animal fluids and tissues. Increasing efforts are exerted to improve the safety of the blood supply such as retrovirus screening using surrogate markers, screening for HIV and other retroviruses with attention to population surveillance for newer agents, cleaner methods of extracting specific blood components by monoclonal antibody techniques and DNA methodologies, development of recombinant DNA products which by-pass the need for plasma derived clotting factors for administration to hemophiliacs. Careful screening of donors, followed by antibody testing, reduces the risk of AIDS and other virus-contaminated blood, but such methods are not foolproof. Such methods require testing supplies and trained technicians which are not available and are too expensive for use in such places as central Africa and other third-world countries where AIDS infects up to onethird of the population. A simpler and less costly method of handling blood is required in such areas of the world.

A photodynamic method has also been evaluated as a means of eradicating viral contaminants (Matthews, J. L. et al., Transfusion, 28,1 1988) but has not been proved to be generally effective and safe. While Factor VIII products may be rendered non-infectious by heat or solvent-detergent methods, no methods are known to guarantee the safety of whole blood or cellular components or plasma. For the whole blood recipient, however, the only reasonably reliable safety procedures are programs allowing for self donation prior to elective surgery by the donor and the use of blood from designated donors, but such programs are incredibly difficult logistically. In spite of heroic efforts to meet the challenge of virus contaminated blood supply, an imperative need continues to exist for a method for treating whole blood for use in transfusion.

It is apparent from the foregoing discussion that a method of killing or inactivating pathogenic viruses in organs, tissues, cell and fluids intended for transfusion or transplantation would be an enormous advance in medicine. It is to this major national and worldwide health care challenge that the present invention is directed.

My copending U.S. patent application Ser. No. 07/290,161, Filed Dec. 28, 1988, describes and claims a method for inactivating virus in blood samples using glycyrrhizic triterpenoid compounds.

The invention described and claimed herein is an improvement thereof and is based upon the discovery of unique synergistic improvement results when glycerol, even trace amounts of glycerol, are combined in the blood or blood product sample with glycyrrhizic triterpenoid compounds.

Further, the invention described and claimed herein is an improvement thereof and is further based upon the discovery of unique synergistic improvement results when even trace amounts of ethylene diamine tetraacetic acid or salts thereof (EDTA), are combined in the blood or blood product sample with glycyrrhizic triterpenoid compounds.

SUMMARY OF THE INVENTION

The invention is embodied, inter alia in an improved transfusion blood container for the introduction of one or more blood products, such as whole blood, platelet concentrations, leukocyte concentrations, plasma, plasma derivatives, whole blood fractions, and combinations thereof, for transfusing the patient, the invention comprising an improved transfusion blood product container and an amount of one or more glycyrrhizic triterpenoid compounds sufficient to comprise from 0.05 to 10.0 wt/%, preferably from about 0.5 to about 3 wt/% and a viral inactivation enhancer, e.g. glycerol or EDTA, or both, of the contents of the improved container when full of the blood product(s), sufficient to substantially inactivate viruses contained in the blood product introduced into said improved container. There is a striking synergism between the glycerol and the glycyrrhizic triterpenoid compound(s) rendering the combination surprisingly effective in inactivating susceptible viruses which may be in the blood product. Even such trace amounts of glycerol as would be ineffective as viral inactivator constitutes in blood products enhance the viral inactivation value of GTPD many fold.

This invention relates to improved containers for collecting and treating whole blood with GTPD compounds, e.g. glycyrrhizic acid, its analogues such as carbenoxolone and cicloxolone, analogues thereof and the salts, esters and other derivatives thereof, and a viral inactivation enhancer, e.g. glycerol or EDTA, or both, and to whole blood for transfusion containing such compounds which is free of CMV virus capable of infecting the recipient of such blood. Inactivation of other viruses found in animal fluids and tissues also results.

This invention is embodied inter alia in improved methods of treatment of mammalian cells and fluids with one or more of a class of compounds referred to here as glycyrrhizic compounds, exemplary of which are glycyrrhizin, glycyrrhizinic acid or glycyrrhetinic acid glycoside, and analogous triterpenes, e.g. carbenoxolone and cicloxolone and their derivatives, and a viral inactivation enhancer, e.g. glycerol or EDTA, or both, to inactivate virus found in animal fluids and tissues, such as cytomegalovirus, bovine diarrhea virus, human immunodeficiency virus and hepatitis viruses.

This invention involves improved methods and improved containers for collecting and treating transfusion blood products, i.e. blood products derived from transfusion quality whole blood, including whole blood as one such product, with GTPD compounds, e.g. glycyrrhizic acid, its analogues such as carbenoxolone and cicloxolone, analogues thereof and the salts, esters and other derivatives thereof and a viral inactivation enhancer, e.g. glycerol or EDTA, or both,, and to whole blood for transfusion containing such compounds which is free of CMV virus capable of infecting the recipient of such blood. Inactivation of other viruses found in animal fluids and tissues also results. At least one of the retroviridae is susceptible to the treatment of this invention, according to presently available data. The most notorious of the retroviridae, HIV-1, the only virus thus far identified as inducing AIDS in humans, is inactivated and/or killed using the improved methods and compositions of this invention. Other retroviridae are considered to be susceptible to the present invention, and treatment to prevent transmission of retrovirus-infected organs, tissues, cells and fluids is within the scope of this invention. The treatment of such organs, tissues, cells and fluids to prevent the transmission of hepandnaviridae-related infections, e.g. hepatitis, is also within the scope of this invention, but data regarding the actual effect of treatments on hepatitis infectivity is so difficult to obtain that reliable data proving the efficacy of the present invention in hepatitis infection inhibition are extremely difficult to obtain.

This invention is embodied in the process of collecting blood from a donor comprising withdrawing the blood from the donor and introducing the blood into a whole blood container which contains an effective amount of a GTPD compound consisting essentially of glycyrrhizin, glycyrrhetinic acid, carbenoxolone, cicloxolone and analogues and derivatives thereof, or mixtures thereof, and one or more viral inactivation enhancers, e.g. glycerol or EDTA, or both, for inactivating HIV and other viruses found in animal fluids and tissues and preventing coagulation of the collected blood.

This invention is also embodied in commercial blood containers which contain an amount of a GTPD compound which consists essentially of glycyrrhizin, glycyrrhetinic acid, carbenoxolone, cicloxolone analogues and derivatives thereof, or mixtures thereof in combination with at least one viral inactivation enhancer, e.g. glycerol or EDTA, or both, in an amount effective to inactivate HIV and/or other viruses found in animal fluids and tissues.

DESCRIPTION OF THE PREFERRED EMBODIMENT

Glycyrrhizic acid, 20B-carboxy-11-oxo-30-norolean-12-en-3B-yl-2-OB-D-glucopyranuronsyl-α-D-glucopyranosiduronic acid, commonly known as glycyrrhizin, glycyrrhizinic acid or glycyrrhetinic acid glycoside (also referred to as biosone, enoxolone, and glycyrrhetin) an extract from Glycyrrhiza, better known as licorice, an extract of the dried rhizome and roots of Glycyrrhiza glabra, is a triterpene and is exemplary of the triterpenes to which this invention relates. Analogous triterpenes to which this invention relates include carbenoxolone and cicloxolone. This invention thus relates to glycyrrhizic acid and analogues thereof, in the form of acids, salts, esters and other derivatives. Many such derivatives are known, such as, for example, glycyrrhetinyl stearate; monopotassium glycyrrhetin; potassium glycyrrhetinate; 11-deoxoglycyrrhetinic acid hydrogen maleate sodium salt; α-D-glucopyranosiduronic acid monoarginine glycyrrhizinate; 18α-Glycyrrhizic acid monosodium salt; 18-α-Glycyrrhizic acid monopotassium salt; disodium 18-α-glycyrrhizate; glycyrrhizinic acid mono(triethanolamine) salt; trisodium glycyrrhizinate; sodium glycyrrhizate; ammonium glycyrrhizinate; sodium carbenoxolone (biogastrone; glycyrrhetinic acid hydrogen succinate disodium salt); and acetylglycyrrhetic acid (glycyrrhetinyl acetate). Glycyrrhizin and the virucidal analogues and derivatives thereof are referred to for convenience herein as glycyrrhizic triterpenoids abbreviated GTPD.

Ring-substituted derivatives of GTPD compounds are contemplated and are included in this invention. Halogen ring substituents, such as, for example, fluoro- and chloro- substituents, sulfate and other active and/or inactivating substituents to the ring structure of GTPD compounds are specifically included in this invention, without excluding other ring-substituted derivatives of GTPD compounds.

In addition to its use as a flavoring agent, licorice has long been a common folk medicine for the treatment of sore throats. While not widely known, various extracts of and preparations derived from licorice, e.g. glycyrrhizin and its derivatives, principally the salts of glycyrrhizic acid, have also been used to a limited degree for many years as an orally administered medication for the treatment of peptic ulcers (Chandler, R. F., *Can. Pharm. J.*, V118, No. 9, 1985), and oral administration of glycyrrhizin contemporaneously with saponin antiinflammatory agents has been reported to inhibit saponin and saponigen hemolysis (Segal, R. et al., *Biochem. Pharmacol.* 26, 7 1977).

GTPDs have been evaluated extensively in vitro, and have been administered orally, intramuscularly and intravenously. No significant toxicity from limited, short term administration of glycyrrhizin has been reported. Adverse reactions have been reported in certain instances of prolonged oral ingestion and a slight relapse after rapid discontinuation of intravenous administration of Stronger Neo-Minaphagen C (SNMC) solution, glycyrrhizin (0.2%), cysteine (0.1%) and glycine (2%) was attributed to the steroid ring in glycyrrhizin (Fujisawa K. et al., *Asian Med. J.* (Japan), 23, 10 1980). Dosages of SNMC as high as 60 ml/day (~12 mg/dy of glycyrrhizin) have been reported (Iwamura K., *Therapiewoche* (W. Germany) 30, 34 1980).

Inactivation of viruses, in vitro, under certain conditions, has been reported (see, e.g., Pompei R., *Exprientia* (Switzerland) 36/3 1980). Such anti-viral activity as GTPD compounds sometimes exhibit has been attributed to reverse transcriptase-inhibitory activity (Nakashima, H. et al., *Jpn. J. Cancer. Res.* 78, 8 1987) and to enhancement of interferon-gamma production (Shinada, M. et al., *Proc. Soc. Exp. Biol.* 181, 2 1986), but the exact mechanism of the anti-viral function has not been confirmed.

Dargan, D. J., and Subak-Sharpe, J. H., (J. Gen. Virol., 1985-1986) reported antiviral action of carbenoxolone and cicloxolone on herpes simplex virus. Their dose-response experiments showed cicloxolone sodium or carbenoxolone sodium interfered with the HSV replication cycle and reduced the infectious virus yield by 10,000- to 100,000-fold, cicloxolone being the more potent anti-herpes agent, but no consistent effect on HSV DNA synthesis was identified. Some inhibition of cellular DNA synthesis was observed, but this was relatively slight.

Csonka, G. W. and Tyrrell, D. A. (*Br. J. Vener. Dis.* 1984, 60 (3) p178) undertook a double blind clinical study to compare the efficacy of carbenoxolone and cicloxolone creams with placebo in initial and recurrent herpes genitalis and reported significant differences in the time to disappearance of pain and the healing of lesions using cicloxolone, but carbenoxolone showed insignificant beneficial effect.

GTPDs have also been evaluated therapeutically as anti-viral agents in the chemotherapy of acquired immune deficiency syndrome (AIDS) (Ito, M., Yamamoto, N., *Yakaguaku Zasshi* (Japan) 188, 2 1988), treatment of EpsteinBarr virus (EBV) infections (Van Benschoten, M. M., *Am. J. Acupunct*, 16, 1 1988), and in the treatment of chronic hepatitis (Fujisawa, K. et al., *Asian Med. J.* (Japan), 23, 10 1980).

The anti-viral activity of GTPDs varies so unpredictably as to preclude any generalized statements as to whether such compounds have general antiviral effect or even as to whether such compounds will generally have antiviral value as to any given virus. While GTPD drugs do, in some environments and under some conditions, exhibit some activity against some viruses, no anti-viral therapy based on GTPDs or in vitro anti-viral application of GTPDs has been generally accepted. The AIDS-causing viruses, HIV-I and HIV-II, are the first retroviruses identified as pathogenic in man. While HIV are more fragile than most infectious viruses and are susceptible to destruction by most virus-inactivating methods, such as heating, use of glycerol compounds, etc., these methods also damage cells, e.g. the red blood cells, and, therefore, are not suitable for use in treating blood. In addition, any substance added to blood will, unless removed, remain in the blood, and must, therefore, be non-toxic when administered intravenously. Removal of added toxins from blood is, at best, complex and expensive and may not be feasible or possible without serious damage to blood components. It has now been discovered that glycyrrhizin, glycyrrhetinic acid, carbenoxolone and cicloxolone and the analogues thereof not only inactivate HIV in blood and are known to be well-tolerated intravenously but, in some instances, also serve as effective anticoagulants and cell-stabilizers and do not interfere with standard blood analyses.

The preferred method of carrying out the invention comprises providing a transfusion blood product container which contains an amount of the GTPD compound, e.g. glycyrrhizin, glycyrrhetinic acid, carbenoxolone or cicloxolone to comprise from about 0.005 weight/percent (w/%) to about 10 w/%, generally in the range of about 0.1 to about 3 w/% and a viral inactivator enhancer, e.g. glycerol or EDTA, or both,, of the collected blood product when the container is filled, such amount being sufficient to inactivate CMV and/or other viruses in blood product collected therein from a donor, and substantially filling the container with the donor's blood product. If the GTPD is to be used as the sole anticoagulant, a quantity sufficient to result in at least about 2 wt/% of the collected blood product should be in the collection container. The collected blood product is held for a sufficient period of time, e.g. 15 minutes or more at normal room temperatures or for an hour or more at near 0° C., to assure that CMV is inactivated before the blood product is administered by transfusion to the recipient patient. Careful admixing is essential and is preferably conducted immediately after the first mixing of blood product and GTPD's.

In carrying out this method, conventional blood product collection containers are used. Such containers are typically made of sterile polymer film and contain an anticoagulant. The collection, handling and administration of the blood product by transfusion is the same as is conventionally carried out, save only for the processes involving preparation of the blood product to containing the GTPD compounds.

The GTPD compounds of this invention may be added to conventional anticoagulants, e.g. citrate dextrose, citrate phosphate dextrose, EDTA, heparin, etc. to enhance the anticoagulant effect of these, or to replace, in whole or in part, such anticoagulants.

There is no criticality respecting the addition of GTPD compounds at the time of collection, as, for example, introducing blood product into bags containing GTPD compounds, though there are some advantages of convenience in this approach and this approach reduces the risk to blood product handlers after collection. GTPD compounds may be added after collection any time in the chain of handling the blood product. It may be desirable to assure a satisfactory inactivation of pathogenic virus in blood product to add GTPD compounds at two or more stages, such as at the time of collection and 24 or 48 hours later, or at any later time. If the blood product is to be used for immediate transfusion, however, one careful thorough intermixing of a higher concentration of GTPD compounds with a shorter delay between collection and transfusion than would normally occur in the routine handling of blood product.

The method of this invention is enhanced and the speed of virus inactivation is increased and the ultimate level of inactivation is improved by including the step of maintaining the temperature of the blood product at from about 27° C. to about 60° C. if the blood product does not contain erythrocytes and to about 45° C. if the blood product contains erythrocytes, or other heatsensitive components. The warming (or maintaining original warmth) ia carried on for at least about one hour, and as high as twenty four hours, or more, though longer heating does not significantly improve the viral inactivation and is equivalent to up to twenty four hours insofar as the virus inactivation is concerned. Temperatures of from about 37° C. to about 42° C. are presently considered optimal for maximum enhancement of virus inactivation in blood products which contain erythrocytes or other heat sensitive constituents. Times as low as about one hour to twenty four hours are considered optimum. There is an inverse relationship between time and temperature. Thus, a shorter time is required at about 45° C. than at 27° C. While longer times would be considered equivalent, as to virus inactivation, it is considered unwise for other reasons, e.g. increased tendency toward hemolysis, to maintain the temperatures in the ranges indicated for more than about 24 hours. A convenient time period is about 12-16 hours, e.g. overnight and a temperature of about 37° C.±about 8° C. is considered optimum for blood products which contain red blood cells. The blood product may be maintained at the indicated temperature soon after collection, just before transfusion, or at any other time after the blood product and glycyrrhizic triterpenoid are mixed.

Illustrative, but not limiting, of one aspect of the invention, 1-MRC-5 cells (Bartels) were grown in FCS and Eagle's minimal essential medium with 50 μg/ml of gentamicin, as the starting cell medium. 2-Cytomegalovirus [ATCC;10$^7$ tissue culture infectious dose (50)] was added to three samples each of (a) the media, (b) blood A and (c) blood B. Glycyrrhizin in DMSO was added to one of the (a), (b) and (c) samples to a final concentration of 2 wt/%. Controls containing only media added to the same volume and DMSO in media were prepared. Six-hundred fold dilutions were used to infect MRC-% monolayers grown in glass coverslips inside glass vials. The inoculum was centrifuged at 1,000Xg for 1 hr. at room temperature, and 1 ml of fresh media was added to each vial. The cultures were incubated at 37° C. and observed daily for cytopathic effect. Seven-days post-infection the monolayers were fixed with methanol and stained by indirect fluorescent method using a CMV monoclonal antibody (Syva). No cytopathic effect was observed in the samples in which glycyrrhizin was present, while 3-4+cytopathic effect was observed in the other samples. The fluorescent antibody technique showed no evidence of residual virus in blood treated with GTPD. Blood mixed with DMSO, and blood in media, tended to clot. Blood mixed with the glycyrrhizic compound did not clot, but slight hemolysis may have occurred. pH adjustments using KOH or NaOH, etc., may be required.

Of the readily available GTPD compounds, carbenoxolone is preferred for its anti-viral effectiveness; however, carbenoxolone solutions are not stable for long periods of time and should be used freshly prepared. In addition, carbenoxolone lacks the powerful anti-coagulant effect which, surprisingly, is exhibited by glycyrrhizin and cicloxolone. Thus, with carbenoxolone the user should include a proved anti-coagulant, the effect of which is enhanced by the carbenoxolone.

It has been established with reasonable confidence that cicloxolone is less effective than carbenoxolone as an anti-viral agent in blood product. On the other hand, however, cicloxolone and glycyrrhizin exhibit very surprising anti-coagulant effect, and, in addition are stable over relatively long periods of time in solution.

Having this discovery to build upon, it is apparent that an effective mode of carrying out the present invention is to provide a mixture of carbenoxolone with either, or both, of glycyrrhizin or cicloxolone, thus obtaining both anti-viral anti-coagulant activity. If desired, anti-coagulant activity may be enhanced with other anti-coagulants, as mentioned above.

A most unusual phenomenon not suggest in any literature of which the inventor is aware was discovered which may be used to great advantage in handling blood product supplies, and is useful in other facets of the invention as well. When GTPDs are added to whole human blood product containing substantial amounts of lipids and lipoproteins the GTPD's are, over a period of time, absorbed or adsorbed or otherwise removed from solution as active compounds. It is, accordingly, possible to treat blood product with an amount sufficient to inactivate the virus, e.g. CMV, in the blood product. Then, by delaying transfusion of the thus treated blood product for a sufficient period of time the blood product may be transfused into the recipient free of such modest toxicity which GTPD's in the concentration ranges under consideration may otherwise introduce into the blood product. The precise mechanism for this removal of GTPD compounds from the blood product solution has not been elucidated with certainty; however, it is presently believed that the GTPD's are absorbed by the lipid or lipoprotein layers on red blood cells or otherwise available in the blood. It is believed, also, that a particular class of lipoproteins is either particularly active in removing GTPD compounds from solution or, perhaps, are uniquely capable of such action. These postulated explanations are offered to aid in understanding and have not been firmly established, however, and the efficacy of the invention is not dependent upon the described action or upon any other postulated mode of action.

Another very significant discovery was made in the course of the investigation of GTPD compounds in blood. It was discovered that the presence of GTPD's very significantly increased the clarity of plasma and sera. A clear separation resulted from the plasma or serum and a layer believed to comprise lipids and/or lipoproteins which, in the absence of GTPD's, gave the plasma or serum a cloudy, translucent appearance. Plasma and serum collected from blood to which GTPD's had been added was crystal clear and transparent.

The GTPD compounds may be used in their acid form, as blood is a very potent buffer; however, it is always necessary to check the pH after adding the GTPD compound and, if necessary, adjust the pH to about 7.0-8.0, e.g. with NaOH or KOH, before using the blood, as certain acid form GTPD compounds drop the pH of blood and plasma significantly to the pH 4-5 range.

The acid form of the GTPD compounds is only slightly soluble in water but is quite soluble in dimethyl sulfoxide. The salt, e.g. ammonium, sodium or potassium salts, of the GTPD compounds are, generally, soluble in water, the sodium and potassium salts being more soluble than the ammonium salts. It is, thus, convenient to purchase or prepare the GTPD compounds as sodium or potassium salts.

One to the most surprising aspects of this invention is the discovery that the addition of an appropriate concentration of GTPD compound(s) to blood tends to stabilize erythrocytes against lysing and other damage.

It has also been discovered that blood treated as described above, when fractionated to produce plasma, clarifies the plasma, eliminating the translucence characteristic of most plasma.

Further, standard blood analyses, e.g. serum protein electrophoresis, basic blood chemistry tests, and lipid tests were unaffected by the presence of the GTPD additives of this invention.

Thus, according to this invention, by a one-step addition of one or more GTPD compounds to blood product at or after the time of collection (if a suitable anticoagulant is used), the red blood cells are not only not lysed, but appear to be stabilized, CMV and other blood-borne viruses, e.g. HIV, are killed or inactivated, plasma is clarified, coagulation is inhibited, and conventional blood analysis are not significantly effected.

It has been established that the exemplary GTPD compounds glycyrrhizin, glycyrrhetinic acid, carbenoxolone and cicloxolone added to a concentration of 1 w/% effectively reduces the CMV content by at least one log, carbenoxolone being about 100 times as effective at the 1 w/% concentration as the other exemplary GTPD compounds. When the concentration of GTPD compound is increased to 2 w/%, glycyrrhizin and cicloxolone each exhibited good anti-coagulant effect, sufficient to permit the omission of any other anticoagulant in most instances, while the limited anti-coagulant effect of carbenoxolone was insufficient. In both instances, however, a one, two or more log CMV inactivation was achieved. In a comparable evaluation, a>3 log kill of HIV was achieved using a 1 w/% carbenoxolone treatment.

A "blind" evaluation was carried out under the direction of the inventor by a scientist with wide experience in CMV infected blood. In this evaluation, carbenoxolone was provided to the scientist with instructions as to preparation of an aqueous solution thereof, but without disclosing the identity of the compound, carbenoxolone, to the scientist. The scientist determined that a 0.5% solution of carbenoxolone in whole blood achieved a 7 log kill, i.e. reduced CMV in the blood by 7 logs (See Jakoby, W. H. and Pastan, I. H. (Eds), CELL CULTURE, (Volume LVIII of "Methods in Enzymology", Academic Press, Inc., New York, Chapter 11, regarding measurement of cell inactivation) in just one-half hour and that 0.25% in blood gave a 2 log kill of CMV. A reciprocal relationship between time and concentration to achieve inactivation of animal fluid or tissue borne virus has now been well-established but only poorly quantified. A concentration of about 0.1 percent present in blood for 12-24 hours is sufficient to achieve substantially total kill or inactivation of CMV. If the blood contains a high EDTA, or both, in, lipid or lipoprotein level, however, it may be desirable to treat the blood with two, three or four timed additions of GTPD's to achieve a certainty of virus inactivation with lower overall additons of GTPD compounds.

The effectiveness of GTPD compounds in killing or inactivating virus has been verified in fetal bovine serum (FBS) where additions glycyrrhetinic acid in concentrations of 0.1 to 0.7 percent followed by adjustment to pH 6.5 and 7.4, respectively for various trials, established a 100% kill of the relatively resistant vesicular stomatitis virus (VSV) was accomplished in all cases.

The effectiveness of GTPD compounds as antiviral agents in blood is, in and of its self, a striking discovery. This discovery that GTPD added as described stabilize red blood cells, and other blood cells such as platelets, inhibit clotting, and stabilize proteins, such as Factor VIII, must be regarded as striking indeed.

The invention is embodied in an article of commerce comprising packaged transfusion blood in a container of whole human blood containing one or more glycyrrhizic triterpenoid compounds in an amount of from 0.005 to 10 wt/%, preferably from about 0.1 to about 3 wt/% and a viral inactivator enhancer, e.g. glycerol or EDTA, or both, effective to substantially inactivate at least cytomegalovirus.

Glycerol and EDTA, most especially glycerol, in combination with GTPD as described gives an unpredicted and unexpected synergism. Glycerol in low concentrations is not an effective anti-viral agent, though at very high concentrations of glycerol, as is true of most hydroxy compounds, may in some instances inactivate some virus. Glycerol plus GTPD when present in concentrations much lower than would provide anything akin to complete viral inactivation with glycyrol alone enhances the viral inactivation power of the GTPD by at least one log and in some instances by three logs or more. The optimum viral inactivator combination, as presently understood, comprises glycyrrhizic triterpenoid compounds in an amount of from 0.005 to 10 wt/%, preferably from about 0.1 to about 3 wt/% and a viral inactivator enhancer, e.g. fatty acid in a concentration of from approximately 0.0001 to 0.5 wt/% of the blood product mixture and preferably a concentration of from approximately 0.0001 to 0.1 wt/% of the blood product mixture.

While other enhancers have not been studied to the extent that glycerol has been, and specific data are still being accumulated, a synergistic amount of 3'-azido-3'-deoxythymidine, dextran, butyl hydroxy toluene, fatty acid or ethylene diamine tetraacetic acid and salts thereof, as well as glycerol, in a concentration of from approximately 0.0001 to 0.5 wt/% of the of the blood approximately 0.0001 to 0.5 wt/% of the of the blood mixture, and preferably in a concentration of from approximately 0.0001 to 0.1 wt/% of the blood product mixture are considered, on the basis of available information and data, to be effective.

The invention is also embodied in a container for collecting, treating, storing, handling or preparing whole human blood or transfusion blood product for transfusion containing, as a part of the container, either in the main container or in a compartment of a multiple compartment container, one or more glycyrrhizic triterpenoid compounds in a concentration of from 0.05 to 10.0 wt/%, preferably from about 0.5 to about 3 wt/% and a viral inactivator enhancer, e.g. glycerol or EDTA, or both, based on blood, sufficient to substantially inactivate virus in a blood product when the container is filled with such product.

Many blood containers have a large compartment for receiving the blood product and one or more side pouches or side containers which have a wall or a closure which, by appropriate physical manipulation, can be opened or ruptured to introduce the contents thereof into the large compartment. Obviously, the nature of the container is immaterial so long as the end result, i.e. a container full of blood product containing the GTPD, can be accomplished with the container. Thus, the invention is embodied in a transfusion blood container for the introduction of one or more blood products, such as whole blood, platelet concentrations, leukocyte concentrations, plasma, plasma derivatives, whole blood fractions, and combinations thereof, for transfusing the patient, the invention comprising a transfusion blood container and an amount of one or more glycyrrhizic triterpenoid compounds sufficient to comprise from 0.05 to 10.0 wt/%, preferably from about 0.5 to about 3 wt/% and a viral inactivator enhancer, e.g. glycerol or EDTA, or both,, of the contents of the container when full of the blood product(s), sufficient to substantially inactivate viruses contained in the blood product introduced into said container.

As a method of collecting blood the invention is embodied in a process comprising introducing said blood into a transfusion blood container containing glycyrrhizic triterpenoid compound sufficient to comprise from 0.05 to 10 wt/%, preferably from about 0.5 to about 3 wt/% and a viral inactivator enhancer, e.g. glycerol or EDTA, or both, of the contents when the container is full.

The invention is also embodied in blood products resulting from the treatment of blood with GTPD compounds. Such derivatives may include, for example, platelet and leukocyte concentrates, plasma, plasma derivatives such as, for example, cryoprecipitate, panels of red blood cells used in blood typing, and blood or blood fractions used for blood analysis such as, for example, the traditional blood samples now routinely collected in vacuum tubes. In such applications, the GTPD compounds may be present in or added to the vacuum tubes or at any later stage, though there are significant advantages in using vacuum tubes containing GTPD compounds. Donor blood may be processed to yield following single-donor components. Multiple donor pools of plasma harvested from whole blood can be processed to yield derivatives such as albumin, plasma protein fraction, Factor VIII concentrate, immune serum globulin preparation and concentrates of other blood factors. GTPD compounds may with great advantage be added along with glycerol or glycerol-water before freezing blood factors or derivatives to obtain a synergistic stabilizing effect, namely the stabilizing of GTPD by glycerol and the stabilizing of the blood factor or derivative, or whole blood in preparing cryoprecipitate, by both glycerol and the GTPD compound(s). GTPD compounds may be used in cell wash solutions to stabilize blood cells, platelets and the like, and to prevent or inhibit coagulation of the cells. It is advantageous, regardless of the mode or purpose in processing blood, to inactivate pathogenic virus at the earliest reasonable stage in the handling chain and/or at specific points in the handling chain. The present invention is well adapted to any blood processing regime.

In all embodiments, the invention exhibits a number of surprising results. The spotty results reported in efforts to determine if, and to what extent, GTPD compounds are indeed virucidal agents led the art to believe, as has been reported, that "the likelihood of developing a blood additive that would kill HIV and HBV and have no effect on laboratory examination of blood seems small."(Peter C. Fuchs, M.L.O., Oct. 1988, 13). In addition, notwithstanding the prior art in which anti-viral activity, to the extent it exists, of GTPD compounds is uncertain, unpredictable and, as yet, unexplained, and the widely accepted proposition that no blood additive could be found which would inactivate blood-borne viruses without adversely effecting the blood, e.g. lysing the red blood cells and/or interfering with blood analyses, the present invention embodies processes and blood compositions in which these desired but hitherto unattainable results are accomplished.

Data indicate that carbenoxolone, over a comparatively short period of time, about an hour or less, is bound by proteins and/or lipids and/or lipoproteins. Such data provide the basis for a nearly ideal method of treatment of solutions and organs for transfusion or implantation is now possible. According to this nearly ideal method, carbenoxolone is added to a fluid, such as blood, blood plasma, tissue culture medium or nutrient, or the like, which contains or to which protein, lipid, or lipoprotein is added, either contemporaneously or subsequently. The virus in the fluid are inactivated immediately, before the carbenoxolone is completely bound, and, thereafter, the carbenoxolone is completely bound. If the protein, etc., is added, the addition can be effected after inactivation of the virus. When the fluid, e.g. blood or plasma, is transfused or the organ transplanted into the donee-patient, the fluid or organ is free of carbenoxolone. While carbenoxolone is welltolerated, the ideal would be to avoid the introduction of any foreign substance not necessary to the in vivo functioning of the fluid or implant organ. This ideal is attainable using the principles of this invention.

The GTPD compounds can be mixed with other active compounds with synergistic results in inactivation of virus. Such synergistic and potentially synergistic compounds include the anti-viral drug 3'-azido-3'-deoxythymidine (AZT), which acts synergistically with the GTPD compounds, dextrans, butyl hydroxy toluene, fatty acids such as oleic acid, chelating agents such as EDTA, and compounds of transition and heavy metals. Highly beneficial effects with minor, if any, adverse side effects have been accomplished using a glycerol, or ethylene diamine tetraacetic acid and salts thereof (EDTA) in very low concentrations of from approximately 0.0001 to 5 wt/%, preferably 0.0001 to 0.01 wt/%.

In the case of blood, plasma or other fluid collection in a bag, vacuum tube, vial or other container, a highly desirable and preferred method and apparatus are utilized. The GTPD compound, in dry form, is in or associated with the container and is dissolved and added to the fluid either immediately before collection or soon afterward. Since some forms of the GTPD compounds decompose in solution, a fresh source of the GTPD compounds is provided by the method just described.

INDUSTRIAL APPLICATION

This invention has direct application in the blood banking industry.

What is claimed:

1. Transfusion blood product comprising a transfusion container containing human blood product and one or more glycyrrhizic triterpenoid compounds in an amount of from 0.005 to 10 wt/% and a synergistic amount of 3'-azido-3'-deoxythymidine, dextran, butyl hydroxy toluene, fatty acid, glycerol or ethylene diamine tetraacetic acid and salts thereof of concentrations of from approximately 0.0001 to 5 wt/% effective to substantially inactivate susceptible viruses found in animal fluids and tissues.

2. The transfusion blood product of claim 1 comprising from about 0.1 to about 3 wt/% glycyrrhizic triterpenoid compounds.

3. The transfusion blood product of claim 2 wherein at least one glycyrrhizic triterpenoid compound is carbenoxolone.

4. The transfusion blood product of claim 2 wherein at least one glycyrrhizic triterpenoid compound is cicloxolone.

5. The transfusion blood product of claim 4 wherein the synergistic amount of 3'-azido-3'-deoxythymidine, dextran, butyl hydroxy toluene, fatty acid, glycerol or ethylene diamine tetraacetic acid and salts is present in a concentration of from approximately 0.0001 to 0.1 wt/% of the blood product when the container is full.

6. A method for preparing human blood product for transfusion, comprising mixing such blood product with one or more glycyrrhizic triterpenoid compounds in a concentration of from 0.05 to 10.0 wt/% and a synergistic amount of 3'-azido-3'-deoxythymidine, dextran, butyl hydroxy toluene, fatty acid, glycerol or ethylene diamine tetraacetic acid and salts thereof of concentrations of from approximately 0.0001 to 5 wt/% based on blood product and holding the resulting mixture for a period of at least about one hour, the concentration being sufficient to substantially inactivate susceptible viruses found in animal fluids and tissues within said time.

7. The method of claim 6 comprising mixing said glycyrrhizic triterpenoid compounds into such blood product in a concentration of from about 0.1 to about 3 wt/%.

8. The method of claim 7 comprising the mixing of the synergistic amount of 3'-azido-3'-deoxythymidine, dextran, butyl hydroxy toluene, fatty acid, glycerol or ethylene diamine tetraacetic acid and salts into such blood product in a concentration of from approximately 0.0001 to 0.1 wt/%.

9. The method of claim 8 wherein the holding time is at least about 12 hours.

10. The method of claim 8 further comprising adding an additional amount of said glycyrrhizic triterpenoid compounds into such blood product approximately at or after the end of the first holding period to renew the concentration thereof to from about 0.1 to about 3 wt/% and holding the resulting mixture for a second holding period of at least about 12 hours.

11. The method of claim 7 further comprising adding an additional amount of said glycyrrhizic triterpenoid compounds into such blood product approximately at or after the end of the first holding period to renew the concentration thereof to from about 0.1 to about 3 wt/% and holding the resulting mixture for a second holding period of at least the same duration.

12. The method of claim 7 further comprising the step of holding the mixture for a further holding time of at least about 12 hours sufficient to permit substantially all of the glycyrrhizic triterpenoid compounds to be removed from solution for substantially eliminating any possible toxicity of the glycyrrhizic triterpenoid compounds to the recipient of the blood product.

13. The method of treating a patient comprising transfusing the patient with blood product comprising one or more glycyrrhizic triterpenoid compounds in a concentration of from 0.005 to 10.0 wt/% and a synergistic amount of 3'-azido-3'-deoxythymidine, dextran, butyl hydroxy toluene, fatty acid, glycerol or ethylene diamine tetraacetic acid and salts thereof in a concentration of from approximately 0.0001 to 5 wt/% based on blood product sufficient to substantially inactivate susceptible viruses found in animal fluids and tissues.

14. The method of claim 13 wherein the synergistic amount of 3'-azido-3'-deoxythymidine, dextran, butyl hydroxy toluene, fatty acid, glycerol or ethylene diamine tetraacetic acid and salts is present in a concentration of from approximately 0.0001 to 0.1 wt/%.

15. The method of claim 14 wherein said blood product comprises glycyrrhizic triterpenoid compounds in a concentration of from about 0.1 to about 3 wt/%.

16. The method of claim 14 wherein the blood product has been retained for a total holding time after being mixed with said compounds of at least about 12 hours sufficient to permit substantially all of said glycyrrhizic triterpenoid compounds to be removed from solution for substantially eliminating any possible toxicity of the glycyrrhizic triterpenoid compounds to the recipient patient.

17. The method of collecting blood product comprising introducing said blood product into a transfusion blood product container containing glycyrrhizic triterpenoid compound sufficient to comprise from 0.005 to 10 wt/% and a synergistic amount of 3'-azido-3'-deoxythymidine, dextran, butyl hydroxy toluene, fatty acid, glycerol or ethylene diamine tetraacetic acid and salts present in a concentration of from approximately 0.0001 to 0.5 wt/% of the contents when the container is full and mixing the contents of the container.

18. The method of claim 17 wherein the synergistic amount of 3'-azido-3'-deoxythymidine, dextran, butyl hydroxy toluene, fatty acid, glycerol or ethylene diamine tetraacetic acid and salts is present in a concentration of from approximately 0.0001 to 0.1 wt/% of the contents when the container is full.

19. The method of collecting blood product of claim 17 wherein the amount of glycyrrhizic triterpenoid compound is sufficient to comprise from about 0.1 to about 3 wt/% of the contents when the container is full.

20. The method of claim 19 wherein the synergistic amount of 3'-azido-3'-deoxythymidine, dextran, butyl hydroxy toluene, fatty acid, glycerol or ethylene diamine tetraacetic acid and salts is present in a concentration of from approximately 0.0001 to 0.1 wt/% of the contents when the container is full.

21. A method for preparing blood product for processing to recover blood constituents, fractions and components, comprising mixing such blood product with one or more glycyrrhizic triterpenoid compounds in a concentration of from 0.05 to 10.0 wt/% and a synergistic amount of 3'-azido-3'-deoxythymidine, dextran, butyl hydroxy toluene, fatty acid, glycerol or ethylene diamine tetraacetic acid and salts is present in a concentration of from approximately 0.0001 to 5 wt/% based on blood product and holding the resulting mixture for a period of at least about one hour, the concentration being sufficient to substantially inactivate susceptible viruses found in animal fluids and tissues within said time and then further processing the blood product to recover blood constituents.

22. The method of claim 21 comprising mixing said glycyrrhizic triterpenoid compounds into such blood product in a concentration of from about 0.1 to about 3 wt/%.

23. The method of claim 22 wherein the holding time is at least about 12 hours.

24. The method of claim 23 further comprising adding an additional amount of said glycyrrhizic triterpenoid compounds into such blood product approximately at or after the end of the first holding period to renew the concentration thereof, the amount being from about 0.1 to about 3 wt/% and holding the resulting mixture for a second holding period of at least about 12 hours.

25. The method of claim 24 further comprising adding an additional amount of said glycyrrhizic triterpenoid compounds into such blood product approximately at or after the end of the first holding period to renew the concentration thereof, the amount being from about 0.1 to about 3 wt/% and holding the resulting mixture for a second holding period of at least the same duration.

26. The method of claim 21 wherein the synergistic amount of 3'-azido-3'-deoxythymidine, dextran, butyl hydroxy toluene, fatty acid, glycerol or ethylene diamine tetraacetic acid and salts is present in a concentration of from approximately 0.0001 to 0.1 wt/%.

27. The method of claim 26 comprising mixing said glycyrrhizic triterpenoid compounds into such blood product in a concentration of from about 0.1 to about 3 wt/%.

28. The method of claim 27 wherein the holding time is at least about 12 hours.

29. The method of claim 27 further comprising adding an additional amount of said glycyrrhizic triterpenoid compounds into such blood product approximately at or after the end of the first holding period to renew the concentration thereof to from about 0.1 to about 3 wt/% and holding the resulting mixture for a second holding period of at least the same duration.

30. The method of any of claims 6, 17, or 21 further comprising the step of maintaining the temperature of the blood product at from about 37° C.±about 8° C. for from about one to twenty four hours after the blood product and the glycyrrhizic triterpenoid compound are mixed.

31. The method of any of claims 6, 17, or 21 wherein the blood product does not contain erythrocytes or other heat sensitive constituents and the process further comprises the step of maintaining the temperature of the blood product at from about 27° C. to about 60° C. for form about one to twenty four hours after the blood product and the glycyrrhizic triterpenoid compound are mixed.

* * * * *